US012336784B2

(12) United States Patent
Gaddipati

(10) Patent No.: US 12,336,784 B2
(45) Date of Patent: Jun. 24, 2025

(54) PALPATION EVALUATION OR DIAGNOSIS DEVICE, SYSTEM AND METHOD

(71) Applicant: VirtuSense Technologies, Peoria, IL (US)

(72) Inventor: Deepak Gaddipati, Peoria, IL (US)

(73) Assignee: VirtuSense Technologies, LLC, Peoria, IL (US)

( * ) Notice: Subject to any disclaimer, the term of this patent is extended or adjusted under 35 U.S.C. 154(b) by 61 days.

(21) Appl. No.: 14/772,042

(22) PCT Filed: Mar. 4, 2014

(86) PCT No.: PCT/US2014/020326
§ 371 (c)(1),
(2) Date: Sep. 1, 2015

(87) PCT Pub. No.: WO2014/134631
PCT Pub. Date: Sep. 4, 2014

(65) Prior Publication Data

US 2016/0015272 A1 Jan. 21, 2016

Related U.S. Application Data

(60) Provisional application No. 61/771,181, filed on Mar. 1, 2013.

(51) Int. Cl.
*A61B 5/00* (2006.01)
*A61H 37/00* (2006.01)

(52) U.S. Cl.
CPC .......... *A61B 5/0053* (2013.01); *A61B 5/4566* (2013.01); *A61B 5/4827* (2013.01);
(Continued)

(58) Field of Classification Search
None
See application file for complete search history.

(56) References Cited

U.S. PATENT DOCUMENTS 1,538,263 A * 5/1925 Ackerman ............. A41D 19/00 2/169
4,144,877 A 3/1979 Frei et al.
(Continued)

FOREIGN PATENT DOCUMENTS

WO 2011/113101 A1 9/2011
WO WO 2012018543 A2 * 2/2012 ........... A61B 5/1121

OTHER PUBLICATIONS

"Adjoin." Merriam-Webster.com Dictionary, Merriam-Webster, https://www.merriam-webster.com/dictionary/adjoin. Accessed Aug. 6, 2024. (Year: 2024).*

*Primary Examiner* — Matthew Kremer
(74) *Attorney, Agent, or Firm* — Potomac Law Group, PLLC; Vincent M DeLuca

(57) ABSTRACT

A physical therapy or palpation evaluation or diagnosis device, system, and method for evaluating the condition of a patient's body, for example, the spine and/or soft tissue. The physical therapist currently uses palpation to subjectively evaluate the condition of the spine, soft tissue and/or muscle of the patient. The physical therapist assigns a subjective score (from 0-10) based on the stiffness and/or mobility of the vertebrae. If a different physical therapist examines the same patient later in the treatment process, the subjective evaluation from the prior therapist would be difficult to interpret.

2 Claims, 16 Drawing Sheets

(52) U.S. Cl.
CPC .......... *A61B 5/6806* (2013.01); *A61B 5/7278* (2013.01); *A61H 37/00* (2013.01); *A61B 5/407* (2013.01); *A61B 5/7475* (2013.01); *A61B 2562/0247* (2013.01); *A61H 2201/5061* (2013.01); *A61H 2201/5074* (2013.01)

(56) References Cited

U.S. PATENT DOCUMENTS

| | | | | |
|---|---|---|---|---|
| 4,430,759 | A * | 2/1984 | Jackrel ............... | A41D 19/0006<br>2/159 |
| 6,168,569 | B1 | 1/2001 | McEwen et al. | |
| 2003/0214408 | A1* | 11/2003 | Grajales ............... | A61B 5/0002<br>340/573.1 |
| 2007/0167844 | A1* | 7/2007 | Asada .................... | A61B 5/022<br>600/485 |
| 2007/0185390 | A1* | 8/2007 | Perkins ............. | A61B 5/02055<br>600/300 |
| 2008/0171311 | A1* | 7/2008 | Centen ................... | G16H 40/63<br>434/265 |
| 2008/0189827 | A1* | 8/2008 | Bauer .................... | A61B 5/225<br>2/161.2 |
| 2008/0249430 | A1* | 10/2008 | John ...................... | A61B 5/372<br>600/544 |
| 2011/0066078 | A1 | 3/2011 | Sarvazyan et al. | |
| 2011/0224564 | A1* | 9/2011 | Moon ................... | H04W 4/029<br>600/509 |
| 2011/0302694 | A1* | 12/2011 | Wang ..................... | A61B 5/103<br>2/160 |
| 2012/0108918 | A1 | 5/2012 | Jarvik et al. | |
| 2014/0052026 | A1* | 2/2014 | Bishara ................ | A61B 5/0053<br>600/587 |

* cited by examiner

1210

Pain-Force Index Report

Patient / Client: earley, troy
Patient DOB: 1992/12/10 Current Date: 2012/11/16

1220

C1 C5 T8

1230 *Pain-Force Table*

| | C1 | | C5 | | T8 | |
|---|---|---|---|---|---|---|
| **Visit Date** | **Pain** | **Force** | **Pain** | **Force** | **Pain** | **Force** |
| 2012/11/15 | 5 | 11 | 4 | 7.8 | 7 | 13 |
| 2012/11/15 | 5 | 9.3 | 3 | 12 | 5 | 20 |
| 2012/11/15 | 3 | 10 | 1 | 15 | 3 | 29 |
| 2012/11/15 | 0 | 16 | 1 | 16 | 0 | 29 |

*PAIN-FORCE INDEX (PFI) IS CALCULATED PER VERTEBRA, BASED ON THE PATIENT'S PAIN (ON A SCALE FROM 0-10) AND THE FORCE APPLIED BY THE PHYSICAL THERAPIST

PHYSICAL THERAPY SPINE PALPATION ASSESSMENT

PHYSICAL THERAPY SPINE PALPATION ASSESSMENT

PATIENT:

DOB: //
JOINT C4

DATE:

PAIN-FORCE INDEX
30
25
20
15
10
5
0
03/25
03/25

| VISIT DATE | PAIN LEVEL | PAIN LEVEL (POUNDS) |
|---|---|---|
| 2013/03/25 | 3 | 1.85099 |
| 2013/03/25 | 3 | 3.6016 |

PRINT
RETURN TO PATIENT DETAILS

PHYSICAL
THERAPY
SPINE
PALPATION
ASSESSMENT

UNITS:
lb
kg

PALPATION EVALUATION OR DIAGNOSIS DEVICE, SYSTEM AND METHOD

FIELD

A palpation evaluation or diagnosis device, system, and method, for example, for spine palpation evaluation or diagnosis.

BACKGROUND

The physical therapist currently uses palpation to subjectively evaluate the condition of the spine, soft tissue and/or muscle of the patient. The physical therapist assigns a subjective score (from 0-10) based on the stiffness and/or mobility of the vertebrae. If a different physical therapist examines the same patient later in the treatment process, the subjective evaluation from the prior therapist would be difficult to interpret.

Currently, there is no quantitative way to track the status of the patient's improvement over a period of time, as the improvement of the patient is based on the subjective interpretations of one or more physical therapist.

Further, the diagnosis varies between each physical therapist, as each physical therapist interprets what they encounter based on their past experiences. In a typical physical therapy practice, multiple physical therapists attend to the same patient throughout the course of treatment. The inconsistencies in subjective interpretation hamper the treatment process.

SUMMARY

A physical therapy or palpation glove device comprising or consisting of one or more layers of material and one or more pressure sensors.

A physical therapy or palpation glove device comprising or consisting of one or more layers of material and multiple pressure sensors.

A physical therapy or palpation glove device comprising or consisting of one or more layers of material, multiple pressure sensors, and a microcontroller electrically connected to the pressure sensors.

A physical therapy or palpation glove device comprising or consisting of one or more layers of material and multiple spaced-apart pressure sensors.

A physical therapy or palpation glove device comprising or consisting of one or more layers of material and multiple pressure sensors located a particular locations on the glove device.

A physical therapy or palpation glove device comprising or consisting of multiple layers of material and one or more pressure sensors.

A physical therapy or palpation glove device comprising or consisting of multiple layers of material, and multiple pressure sensors, and a microcontroller electrically connected to the multiple pressure sensors.

A physical therapy or palpation glove device comprising or consisting of multiple layers of material and one or more pressure sensors located between the multiple layers of material.

A physical therapy or palpation glove device comprising or consisting of multiple layers of material, multiple pressure sensors, and a microcontroller electrically connected to the pressure sensors, the pressure sensors and microcontroller located between the multiple layers of material.

A physical therapy or palpation glove device comprising or consisting of one or more layers of material and a pressure sensor located in a thumb portion of the glove device.

A physical therapy or palpation glove device comprising or consisting of one or more layers of material and a pressure sensor located in an index finger portion of the glove device.

A physical therapy or palpation glove device comprising or consisting of one or more layers of material and a pressure sensor located in a thumb portion of the glove device and a pressure sensor located in an index finger portion of the glove device.

A physical therapy or palpation glove device comprising or consisting of one or more layers of material and a pressure sensor located in a back hand portion of the glove device.

A physical therapy or palpation glove device comprising or consisting of one or more layers of material and pressure sensors located in a thumb portion, index finger portion, and back hand portion, respectively, of the glove device.

A physical therapy or palpation glove device comprising or consisting of one or more layers of material and a pressure sensor located in a side hand portion of the glove device.

A physical therapy or palpation glove device comprising or consisting of one or more layers of material and pressure sensors located in a thumb portion, index finger portion, back hand portion, and side hand portion, respectively, of the glove device.

A physical therapy or palpation glove device comprising or consisting of one or more layers of material and multiple pressure sensors with one or more pressure sensors located in a thumb portion, index finger portion, back hand portion, respectively, of the glove device, and two or more pressure sensors located in a side hand portion of the glove device. The pressure sensors, for example, can be an Interlink Electronics FSR 402 Force Sensitive Resistors.

The physical therapy or palpation glove device can be made of one or more layers of material (e.g. fabric, Spandex, Lycra (e.g. Lycra Activewear Fabric, 65% cotton, 35% Lycra)). For example, the physical therapy glove device comprises an inner layer (e.g. inner liner) and an outer layer (e.g. outer shell). The inner layer and outer layer can be made of the same material, or different materials.

The physical therapy or palpation glove device, for example, can be made by using a pattern to cut a layer of fabric. For example, the same pattern is used to cut two glove-shape pieces of fabric, which are then placed overlapping and sewn around the perimeter edges thereof. This assembly is turned inside out to form an outer fabric glove (e.g. outer shell). Another pattern slightly smaller is used to form an inner fabric glove (e.g. inner liner). After assembly of the outer shell and inner liner, the inner liner is inserted within the outer shell.

The pressure sensors wired to a microcontroller are inserted between the outer shell and inner line of the glove device. The wiring can be provided before or after placement of the pressure sensors. The pressure sensors are positioned with one pressure sensor in the thumb portion, one pressure sensor in the index finger portion, one sensor on the back hand portion, and two spaced-apart sensors on a side hand portion of the glove device. The pressure sensors can be secured within the glove device by sewing, using adhesive, Velcro, mechanical fastener, or other suitable securing method or device. The microcontroller can be located in the front or back of the hand portion.

The physical therapy or palpation device is for evaluating a patient's spine condition. For example, the physical therapy device is worn by a physical therapist to evaluate the condition of the patient's spine. Specifically, the physical therapy glove device is for measuring the pressure applied to the patient's spine by the physical therapist. For example, the physical therapy glove device can be used to measure the level of pressure applied to the patient's spine when the patient experiences discomfort and/or pain. The physical therapy device is a stand alone device, and can be used in various manners or applications.

In the spine palpation evaluation system, the physical therapy glove device is used in combination with a patient pain indicator device to obtain information regarding when a patient senses discomfort and/or pain.

The patient pain indicator device can be an electronic wireless hand held device for communicating with a microprocessor (e.g. microprocessor of personal computer or laptop) of the spine palpation evaluation system. The physical therapy glove device, for example, can communicate with the same microprocessor.

The patient pain indicator device comprises a housing, one or more buttons (e.g. three), internal electronics for wirelessly communicating with the microprocessor, and an energy supply (e.g. battery). The patient pain indicator device is configured to send a wireless signal to the microprocessor when the patient depresses the main button to indicate when the patient feels discomfort and/or pain.

During a spine palpation evaluation, the patient is provided with the patient pain indicator device. Then, the physical therapist wearing the physical therapy glove device begins applying pressure to the patient's spine. For example, the physical therapist focuses on a particular vertebrae, joint, or group of soft tissue (e.g. muscle group) to apply pressure to using the physical therapy glove device. The physical therapist initial applies low pressure to the particular vertebrae, joint, or group of soft tissue, and then increases the amount of pressure until the patient presses the patient pain indicator device to indicate discomfort and/or pain. The level of pressure is recorded by the microprocessor/computer for this indication of discomfort/pain by the patient for the particular vertebrae, joint or group of soft tissue. The process continues for each vertebrae, joint or group of soft tissue selected to be evaluated. The process can be repeated at the same session and recorded as a second evaluation, or the process can be repeated at a subsequent session to determine the change of condition (e.g. healing) of the patient's spine condition.

A palpation evaluation or diagnosis system comprising or consisting of a physical therapy glove device, a patient pain detector device, and a microprocessor receiving signals from the physical therapy glove device and patient pain detector device.

A spine palpation evaluation or diagnosis system comprising or consisting of a physical therapy glove device, a patient pain detector device, and a microprocessor receiving signals from the physical therapy glove device and patient pain detector device.

A palpation evaluation or diagnosis system comprising or consisting of a physical therapy glove device comprising one or more pressure sensors, a patient pain detector device, and a microprocessor receiving signals from the physical therapy glove device and patient pain detector device.

A spine palpation evaluation or diagnosis system comprising or consisting of a physical therapy glove device comprising one or more pressure sensors, a patient pain detector device, and a microprocessor receiving signals from the physical therapy glove device and patient pain detector device.

A palpation evaluation or diagnosis system comprising or consisting of a physical therapy glove device comprising multiple pressure sensors and a microcontroller, a patient pain detector device comprising a microcontroller, and a microprocessor receiving signals from the physical therapy glove device and patient pain detector device.

A spine palpation evaluation or diagnosis system comprising or consisting of a physical therapy glove device comprising multiple pressure sensors and a microcontroller, a patient pain detector device comprising a microcontroller, and a microprocessor receiving signals from the physical therapy glove device and patient pain detector device.

A method of palpation evaluation or diagnosis comprising applying pressure to a patient's spine by a physical therapist using a physical therapy glove device and generating a signal by a patient when the patient feels discomfort or pain at a particular level of pressure.

A method of spine palpation evaluation or diagnosis comprising applying pressure to a patient's spine by a physical therapist using a physical therapy glove device and generating a signal by a patient when the patient feels discomfort or pain at a particular level of pressure.

A method of palpation evaluation or diagnosis comprising applying pressure to a patient's spine by a physical therapist using a physical therapy glove device, generating a signal by a patient when the patient feels discomfort or pain at a particular level of pressure, and recording a level of pressure and time upon the patient feeling discomfort or pain.

A method of spine palpation evaluation or diagnosis comprising applying pressure to a patient's spine by a physical therapist using a physical therapy glove device, generating a signal by a patient when the patient feels discomfort or pain at a particular level of pressure, and recording a level of pressure and time upon the patient feeling discomfort or pain.

A method of palpation evaluation or diagnosis comprising applying pressure to a patient's spine by a physical therapist using a physical therapy glove device, generating a signal by a patient when the patient feels discomfort or pain at a particular level of pressure, recording a level of pressure and time upon the patient feeling discomfort or pain, and tracking repeat evaluations of the patient over time.

A method of spine palpation evaluation or diagnosis comprising applying pressure to a patient's spine by a physical therapist using a physical therapy glove device, generating a signal by a patient when the patient feels discomfort or pain at a particular level of pressure, recording a level of pressure and time upon the patient feeling discomfort or pain, and tracking repeat evaluations of the patient over time.

The spine palpation evaluation or diagnosis system and method provides a spine palpation assessment (SPA) to standardize the physical therapist evaluations. The SPA captures real-time data of the tactile evaluation sessions to create reports that depict the treatment progress of the patient's spine condition.

The spine palpation evaluation system and method provide a tool that can be used to record and capture how much pressure on a particular vertebrae, joint or group of soft tissue is causing pain. The innovation in SPA lies in the capturing the time (e.g. date) and severity of pain indicated by the patient along with the quantitative reading from the pressure sensors regarding the level of pressure applied by the physical therapist, which caused the pain on a particular vertebrae or location on the patient's body.

For example, a pain score and the pressure reading are combined to create a Pain Force Index (PFI) that can be compared over a time line of treatment to track and show the progress of the patient's treatment and provide quantifiable measurements.

The spine palpation evaluation system and method can be used for training, progress tracking, and rehabilitation in physical therapy, occupational therapy, and use by chiropractors.

The SPA platform enables objectifying the physical therapist's interpretation for palpation-based procedures thereby allowing for standardized patient care. This system and method objectively captures the pressure and time (e.g. date) of a patient's pain, as well as captures the patient's perceived intensity of pain to aid in diagnosis and evaluating treatment progression. This system and method can be used to aid treatment and show the progress of a patient.

Using SPA, multiple therapists can standardize force measurements per individual vertebrae throughout the treatment. This force measurement is combined with the subjective input from the patient using a Numeric Pain Rating Scale (NPRS), when the patient encounters pain on a particular vertebra.

During treatment, the patient is provided with the wireless patient pain indicator device comprising a button to indicate when the patient experiences pain. The combination of force and NPRS is used to calculate the Pain Force Index (PFI) for each vertebra throughout the entire treatment. The Pain Force Index (PFI) is calculated per vertebra of the spine or individual location of a group of soft tissue, based on the patients subjective pain indication based on a NPRS scale and the minimum force applied by the therapist that causes the pain.

The SPA platform aims to standardize palpation based rehabilitation assessments and improve patient care. The system has data logging and PFI comparison to measure the outcomes and quality and effectiveness of the treatment plan. In addition, physical therapists normally document their findings, including information such as vertebra with high/low mobility and any unease or pain the patient encounters, at the end of the entire procedure, which can result in mixed-up vertebrae segments or pain indications. By using the SPA software during an evaluation, the therapist can better document issues in an effective, streamlined fashion.

The same technology can be used to measure the force required to exceed the patient's strength, which is a common physical therapy, and an industrial rehabilitation process.

The objectively recorded data of the patient evaluation can be used to discourage fraud and malpractice, as well as providing better records for insurance companies' audits. Data from SPA can aid in the evaluation of workers compensation claims by quantifying the pressure values, locations and intensities of pain over multiple sessions. This data, when combined with physical therapists interpretation, can be used to determine the validity of a claim. It would be hard to fake pain at the same region, at the same pressure over multiple visits. If the readings are inconsistent during and between visits, this would help to find fraudulent claims of injury. Fraudulent workman's compensation cases can be identified by inconsistent PFI readings over the course of the treatment.

A new trend in the insurance world is to move towards result driven healthcare instead of repeatedly paying for ineffective treatments. SPA can capture objective data for multiple patients over multiple visits based on numerous conditions to prove or disprove the effectiveness of a treatment.

In addition, the data collected from multiple therapy centers by multiple therapists on different patient groups can be subcategorized and analyzed to measure efficacy of a therapist, efficacy of an institution, and the efficacy of a particular treatment plan based on age, sex, and problem. This can help to streamline the treatment plans across multiple organizations.

The palpation evaluation or diagnosis system and method can be applied to other parts of the body. For example, the palpation evaluation or diagnosis system can be applied for measuring muscle strength of a worker/patient's hand and/or legs. Manual muscle testing can then be objectified when the therapist wears an SPA glove device and pushes on the patient's body in specific directions. The SPA can measure the peak force needed to break the strength and the time it takes. The maximum forces, body part where the test is administered, and the directions can be stored in a database and compared over population norms and over a period of time with the same patient.

DETAILED DESCRIPTION

Figures 1, 2:
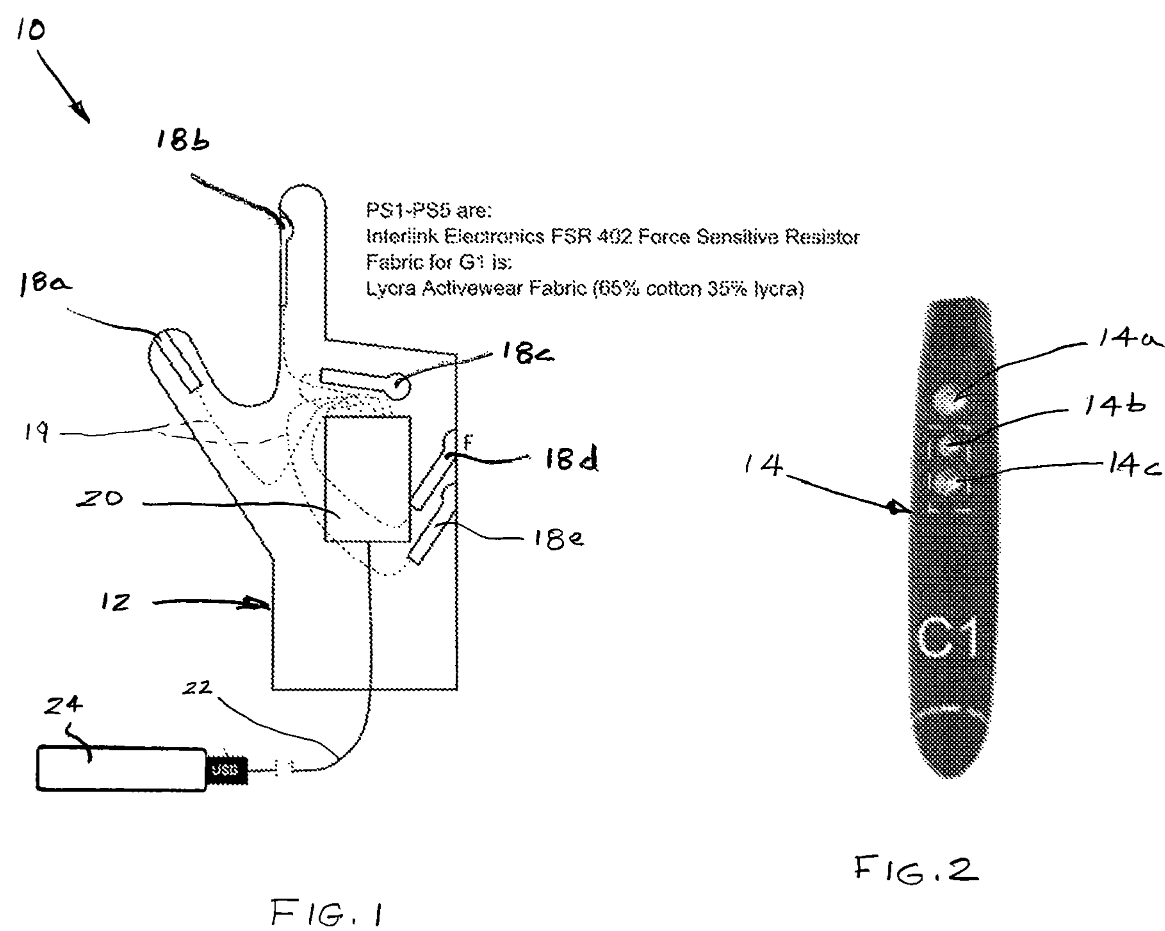
FIG. 1 is a diagrammatic view of a physical therapy glove device connected to a computer.
FIG. 2 is a perspective view of a patient pain indicator device.
Figure 3:
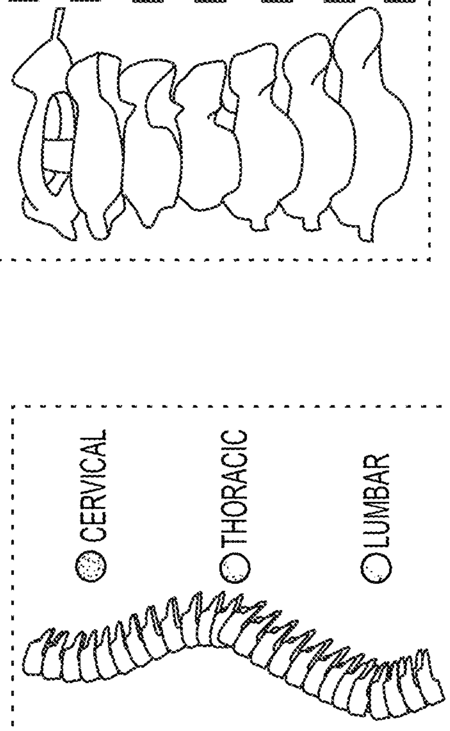
FIG. 3 is a screen shot of a patient demo for evaluating posterior to anterior mobilization.
Figure 4:
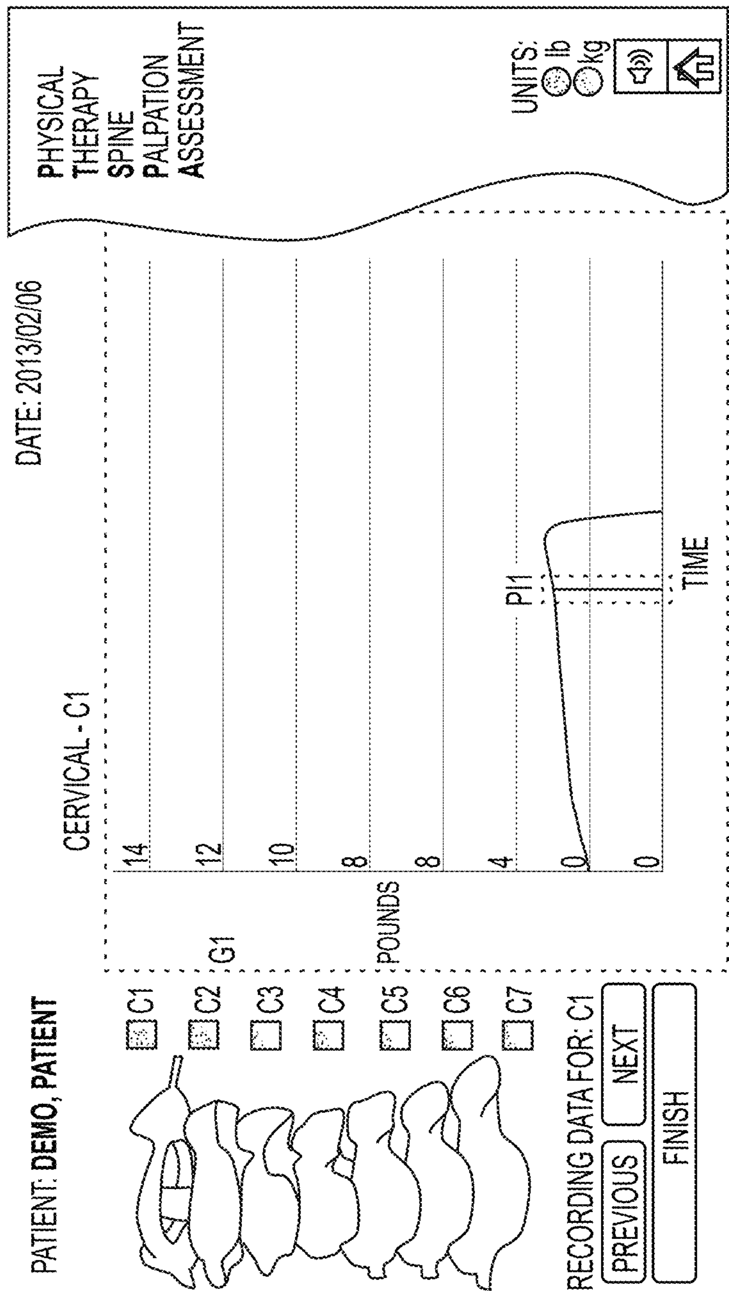
FIG. 4 is a screen shot of a patient demo showing graph pressure applied verses time.
Figure 5:
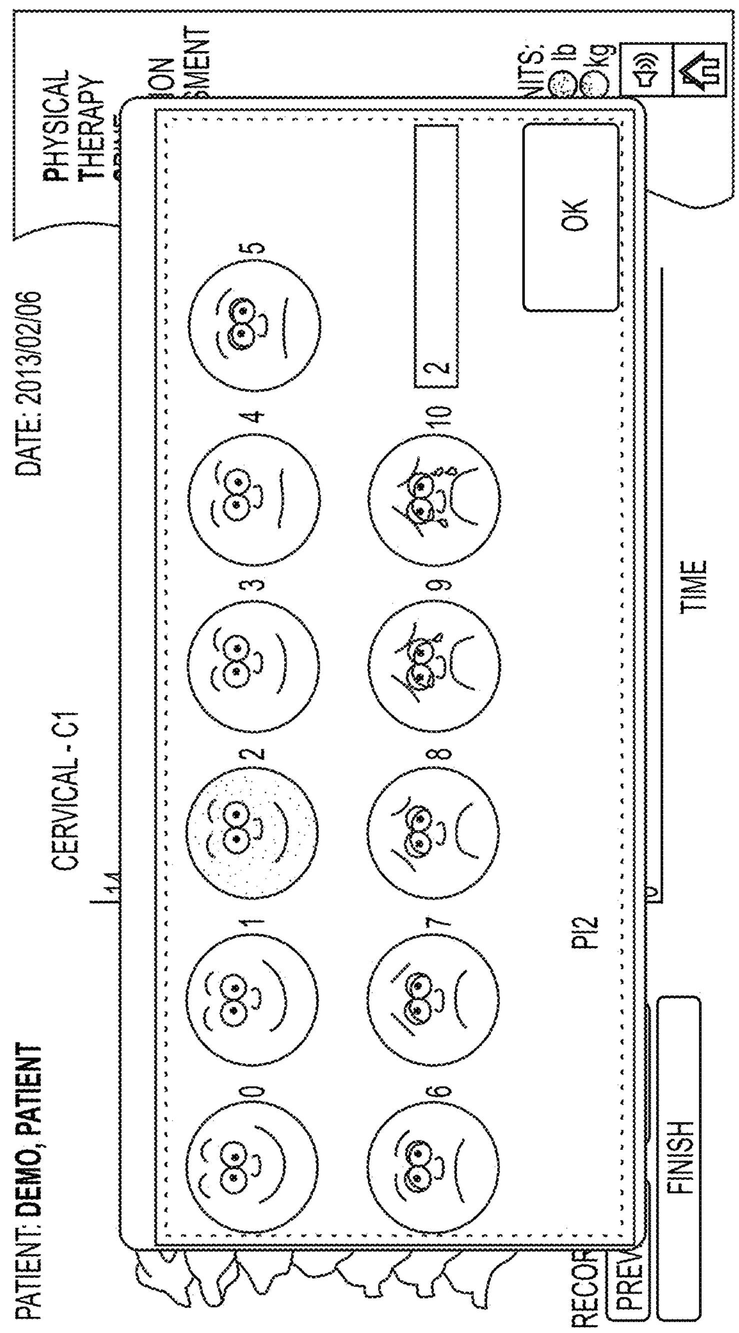
FIG. 5 is a screen shot of a patient demo showing a patient pain level chart.

The Spin Palpation Assessment (SPA) system 10 is shown in FIGS. 1-3. The SPA system 10 comprises a physical therapy glove 12, a patient pain indicator device 14, and a software package 16. The physical therapy glove 12 is shown in FIG. 1, and a patient pain Indicator device is shown in FIG. 2. The input from the physical therapy glove 12 and pain indicator device 14 are recorded using a Graphical User Interface (GUI) software package, as shown in FIGS. 3-5.

The physical therapy glove 12 comprises pressure sensors 18*a*-*e* specifically located on the physical therapy glove 12 to record important interactions that the physical therapist normally conducts. The physical therapy glove 12, for example, can be made of Lycra Activewear Fabric (65% cotton, 35% Lycra. The five (5) pressure sensors 18*a*-*e*, for example, can be five (5) Force Sensitive Resistors (FSR-402) manufactured by Interlink Electronics. The five (5) sensors can be glued and stitched onto the glove near the thumb, index fingers and pisiform area.

The physical therapy glove device 12 can be made of Spandex, a stretchable and breathable fabric, which improves the haptic feeling for the therapists and is tight fitting when the therapist wears the glove. The glove is double-layered to isolate the sensors and electronics from both the therapist and the patient.

The pressure sensors 18*a-e* are connected via wires 19 to a microcontroller 20 (e.g. microcontroller board), which samples the sensor values of the pressure sensors 18*a-e*, and then transmits this data over the USB cable 22 (USB1) to the computer 24. Alternatively, the data can be transmitted wirelessly to the computer 24.

The patient pain indicator device 14, for example, can be a handheld wireless device that acts as a switch to indicated when pain is felt. For example, a button 14*a* can be depressed by a patient to indicate when pain is felt. The button 14*a* is connected to a wireless transmitter along with a microcontroller, which transmits the patient's pain response wirelessly to the computer 24 over a wireless receiver connected to a USB cable.

The software package connects and interprets information from the physical therapy glove device 12 and patient pain indicator device 14, as well as manages the flow of an examination. As shown in FIG. 3, once a therapist selects a patient, they can select to use one physical therapy glove device 12, or two gloves devices for this examination, and select spine (SP) or soft tissue (ST). When the therapist selects spine, he selects what part of the spine (SEL1) and which specific vertebra (SEL2) to examine. As shown in FIG. 4, during the examination, the sensor data is plotted (G1) in real time and any pain indicators (P11) are shown. Once the therapist completes his evaluation of that vertebra, a pain indicator scale screen (PI2) records the intensity of the pain experienced by a patient. The entire session data is stored on the local computer 24, and stored on a server locally or to a cloud connected through a LAN\WLAN.

A wireless switch or remote presentation controller can be used for patient pain indicator device 14. For example, a Powerpoint clicker manufactured by Presenter can be used for the patient pain indicator device 14.

The computer 24, for example, can be a laptop, tablet, or desktop X86 computer with one or more USB ports that can be used to launch the software application. For example, the computer 24 can be a HP Pavilion DV6 laptop.

The computer can be connected to the Internet via an outgoing https to store the data on the cloud and/or a server on the internal network.

The physical therapy glove 12 is worn by a physical therapist when performing a palpation exam of a patient's spine or soft tissue. The physical therapy glove 12 is double layered, to isolate the sensors 18*a-e*, wires 19, and microcontroller board 20 (electronics) from both the physical therapist and the patient. The thumb pressure sensor 18*a* captures the force applied by the thumb, which is usually used on the upper parts of the spine. The side index finger pressure sensor 18*b* captures forces recorded when the therapist palpates with the side of the finger, normally used on the neck. The pressure sensor 18*c* located the back of the physical therapy glove 12, which allows easier progression through the examination. The pressure sensors 18*d*, 18*e* on the side of the hand are positioned to record pressure when palpating in a C-grip fashion, usually used on the lower parts of the spine.

During the exam, the patient is given the patient pain indicator device 14 and instructed to push the button 14*a*, if they encounter pain. This information is transferred to the computer and interpreted by the software package.

The software package interfaces to the physical therapy glove 12 and patient pain indicator device 14, and records data on patients generated during each evaluation session. Once the physical therapist has logged in and entered the necessary information for a new patient, they are brought to the screen shot view shown in FIG. 3. The physical therapist can select what areas of the spine (SEL1) to evaluate, and specify which vertebra is going to be palpated in that area of the spine (SEL2). On subsequent visits this data is auto-populated with the previous selections, but the physical therapist can add or remove vertebra as treatment progresses. When the vertebra to palpate has been selected, the physical therapist selects "continue" and the examination begins.

The examination starts with the first vertebra selected in the list, and proceeds to the next vertebra, until all of the vertebrae have been evaluated. During the examination, the graph of recorded pressures (G1) is shown in real time for the vertebra currently being palpated. If the patient presses the pain button 14*a*, an event is recorded (P11), and the corresponding pressure for that pain is saved. If the pain button 14*a* of the patient pain indicator device 14 is pressed, then the physical therapist presses the pressure sensor 18*c* and the screen shown in FIG. 5 is displayed.

The physical therapist asks the patient to rate the intensity of the pain on the standard scale (P12) shown, and then enters the information either numerically or via mouse selection. At the conclusion of the examination, a report is generated showing the progress of each vertebra over the treatment progress. This report can be referenced in the saved patient history by other therapists, used to determine progress of treatment, or provide information to a third party if necessary.

Figure 6:
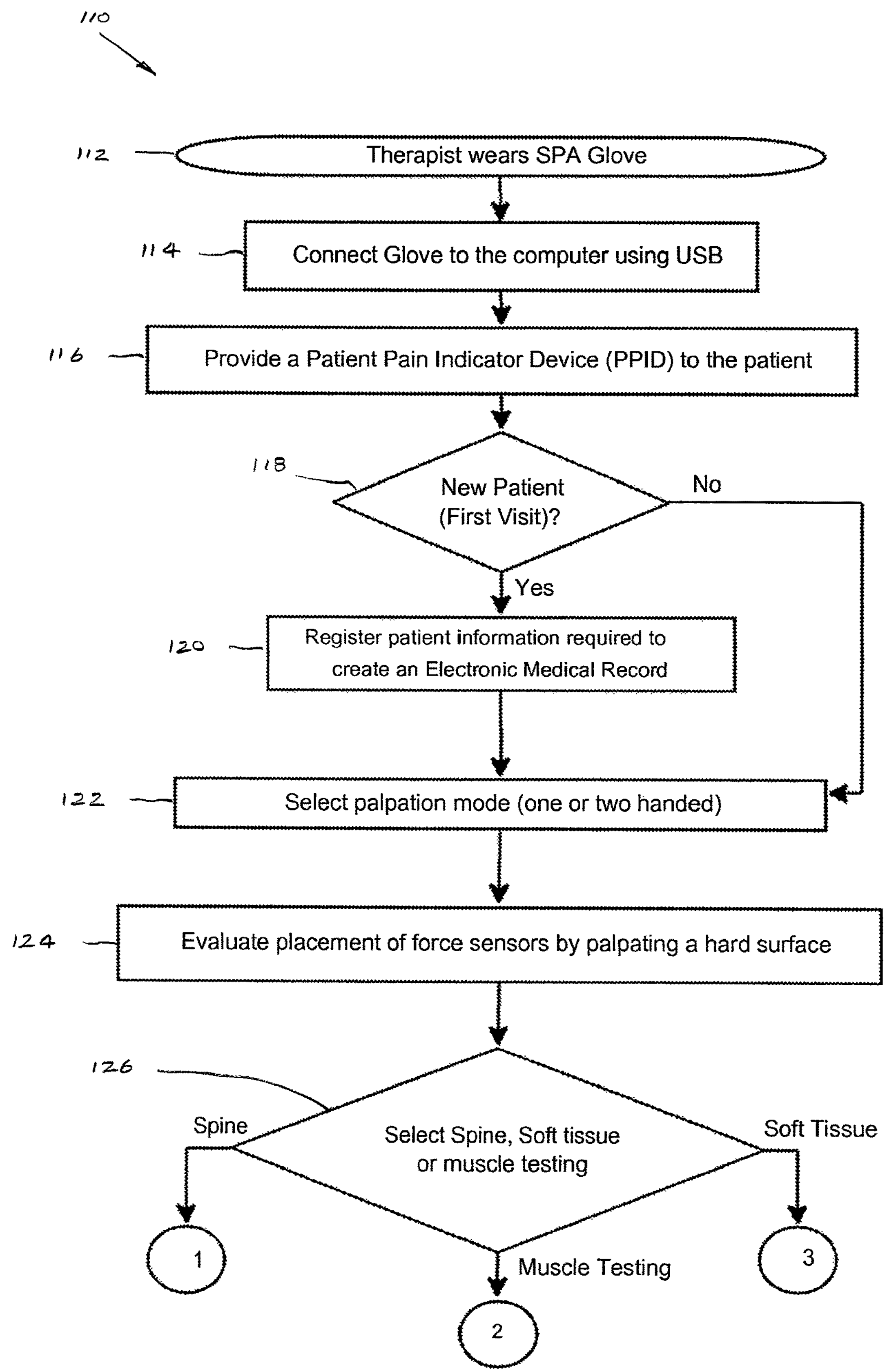
FIG. 6 is a spine evaluation flow chart diagram.

A spine evaluation flow chart diagram 110 is shown in FIG. 6.

The spine evaluation flow chart diagram 110 comprises: Therapist wears SPA Gloves (step 112); Connect Glove to the computer using USB (step 114); Provide a Patient Pain Indicator Device (PPID) to the patient (step 116); New Patient (First Visit)? (decision 118); Register patient information required to create an Electronic Medical Record (step 120); Select palpation mode (one or two handed) (step 122); Evaluate placement of force sensors by palpating a hard surface (step 124); and Select Spine, Soft tissue of muscle testing (decision 126).

Figure 7:
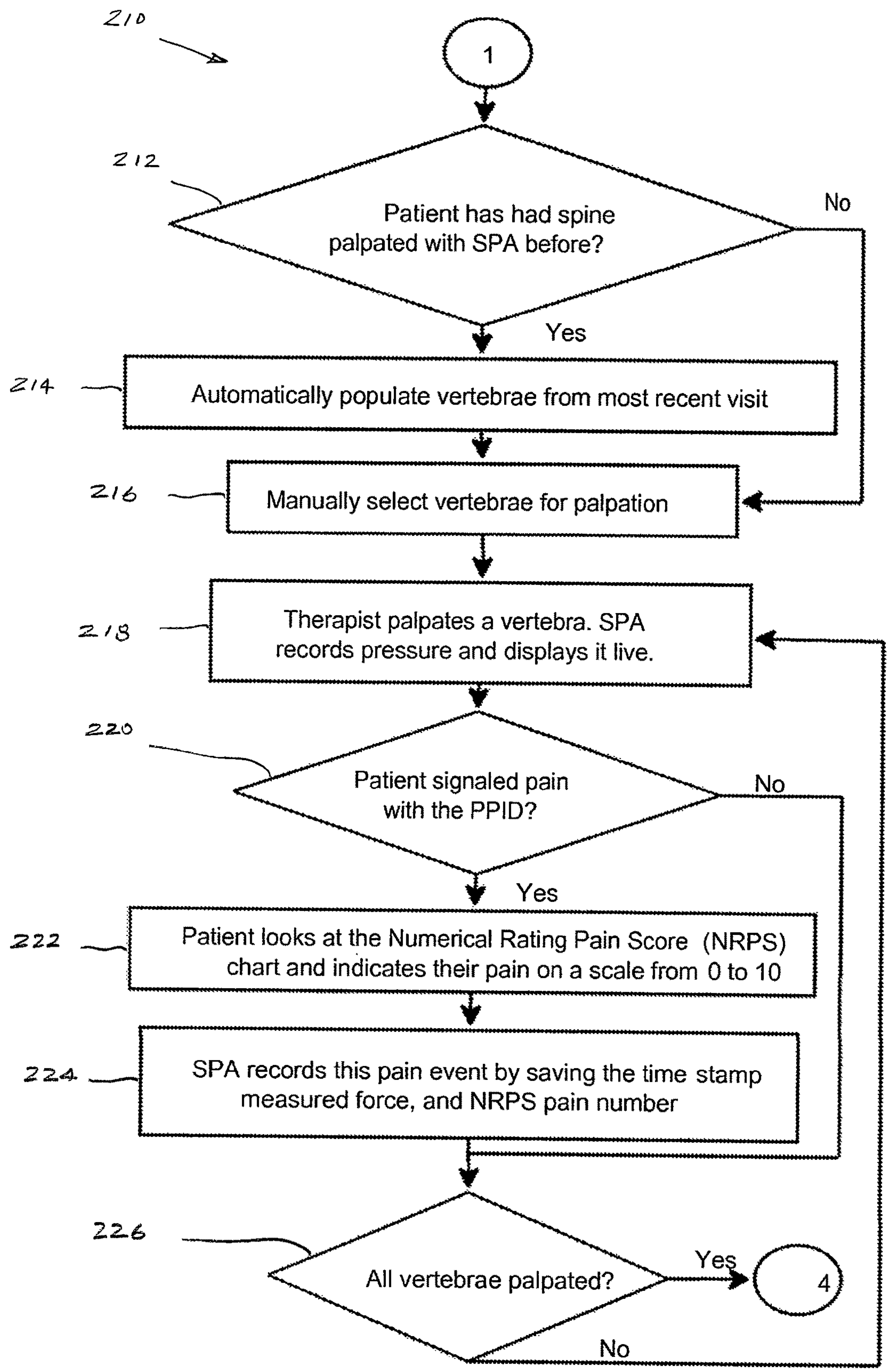
FIG. 7 is a Spine flow chart diagram (Flow Chart "1").

A Spine flow chart diagram 210 (Flow Chart "1") is shown in FIG. 7.

The Spine flow chart diagram 210 comprises: Patient has had spine palpated with SPA before? (decision 212); Automatically populate vertebrae from most recent visit (step 214); Manually select vertebrae for palpation (step 216); Therapist palpates a vertebra. SPA records pressure and displays it live (step 218); Patient signaled pain with the PPID? (decision 220); Patient looks at the Numerical Rating Pain Score (NRPS) chart and indicates their pain on a scale from 0 to 10 (step 222); SPA records this pain event by saving the time stamp measured force, and NRPS pain number (step 224); and All vertebrae palpated? (decision 226).

Figure 8:
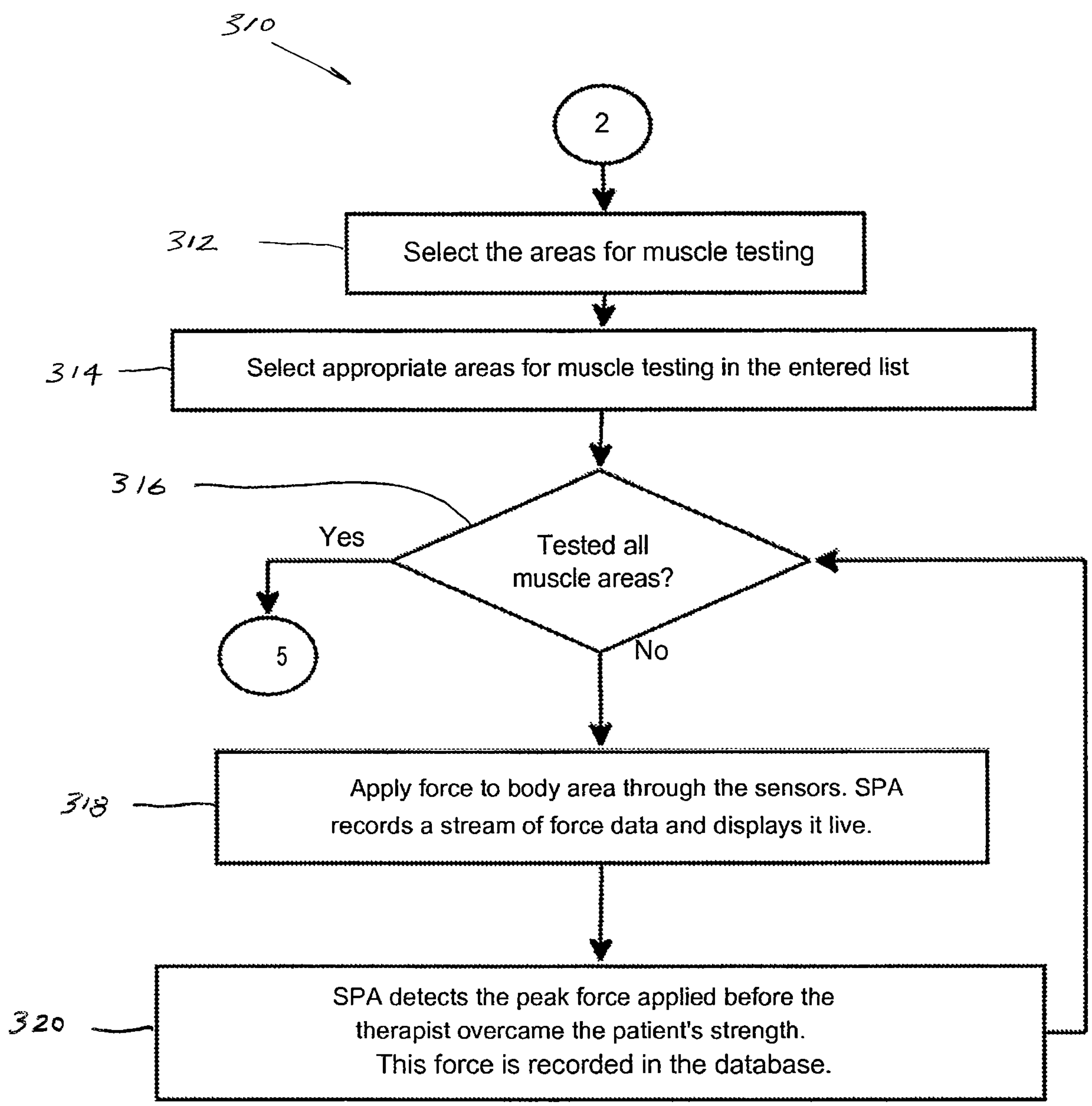
FIG. 8 is a Muscle Testing flow chart diagram (Flow Chart "2").

A Muscle Testing flow chart diagram 310 (Flow Chart "2") is shown in FIG. 8.

The Muscle Testing flow chart diagram 310 comprises: Select the areas for muscle testing (step 312); Select appropriate areas for muscle testing in the entered list (step 314); Tested all muscle areas? (decision 316); Apply force to body area through the sensors. SPA records a stream of force data and displays it live (step 318); and SPA detects the peak force applied before the therapist overcame the patient's strength. This force is recorded in the database (step 320).

Figure 9:
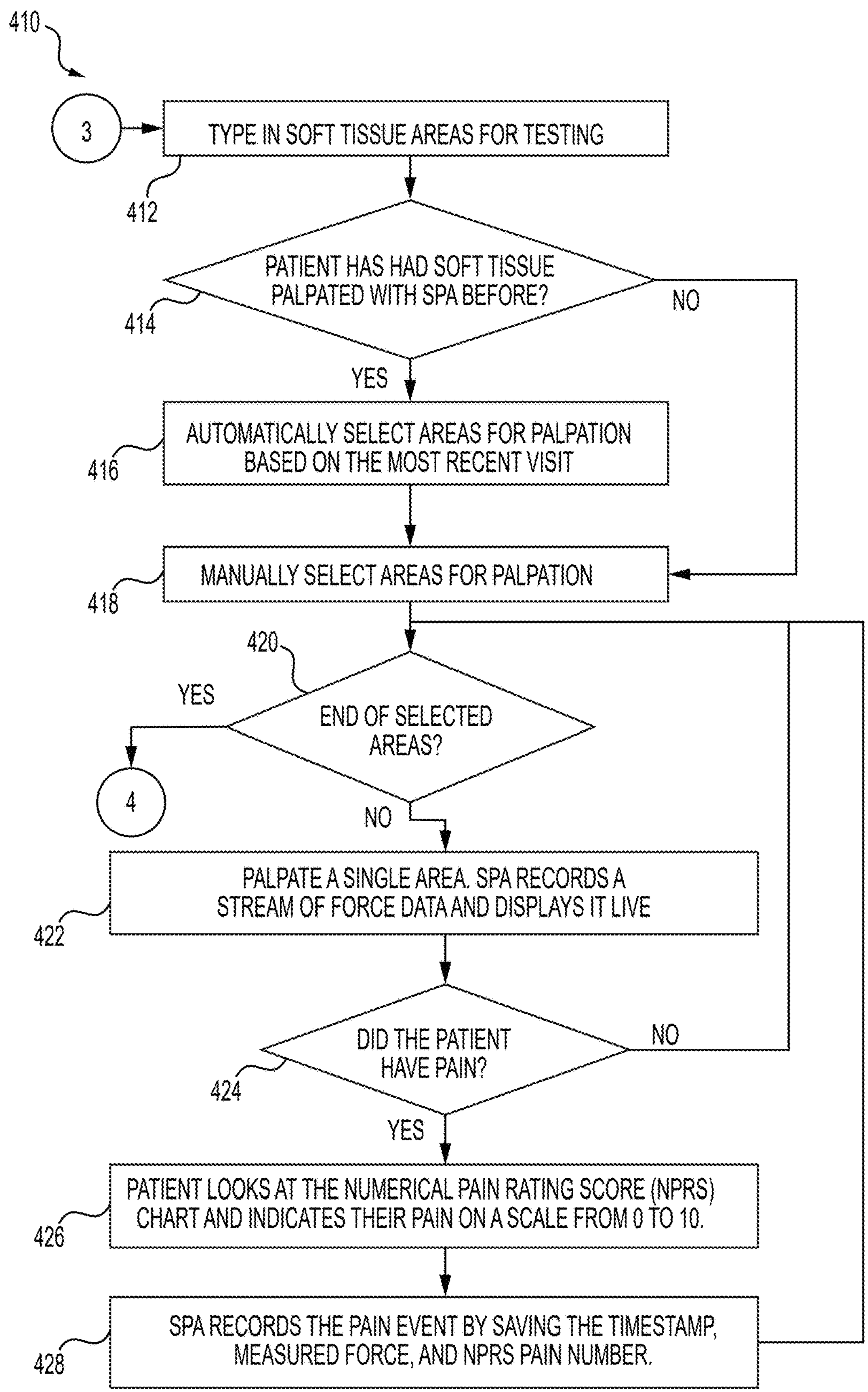
FIG. 9 is a Soft Tissue flow chart diagram (Flow Chart "3").

A Soft Tissue flow chart diagram 410 (Flow Chart "3") is shown in FIG. 9.

The Soft Tissue flow chart diagram 410 comprises: Type in soft tissue areas for testing (step 412); Patient has had soft tissue palpated with SPA before? (decision 414); Automatically select areas for palpation based on the most recent visit (step 416); Manually select areas for palpation (step 418); End of selected areas? (decision 420); Palpate a single area. SPA records a stream of force data and displays it live (step 422); Did the patient have pain? (decision 424); Patient looks at the Numerical Pain Rating Score (NPRS) chart and indicates their pain on a scale from 0 to 10 (step 426); and SPA records the pain event by saving the timestamp, measured force, and NPRS pain number (step 428).

Figure 10:
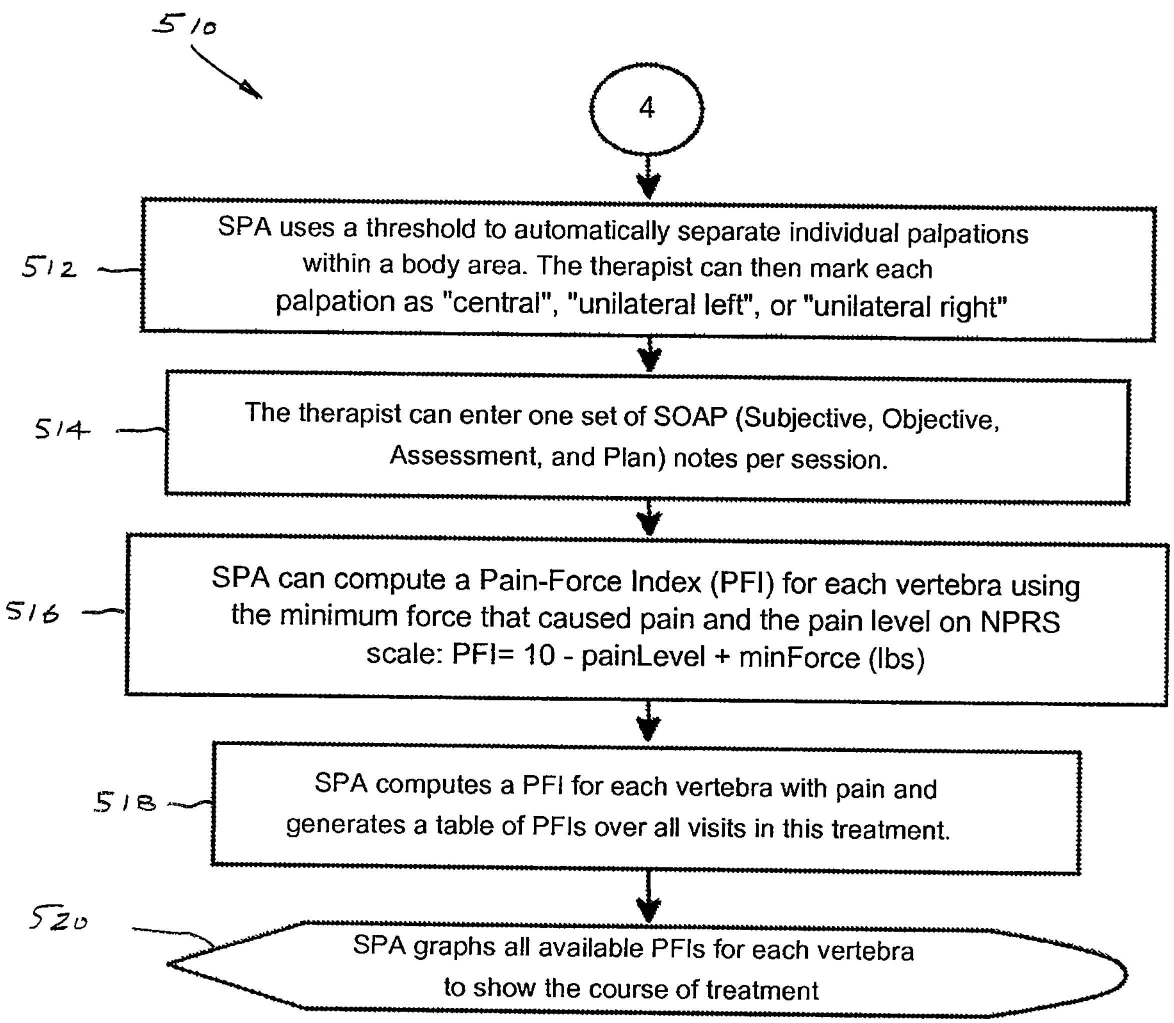
FIG. 10 is a All vertebrae palpated flow chart diagram.

An All vertebrae palpated flow chart diagram 510 (Flowchart "4") is shown in FIG. 10

The All vertebrae palpated flow chart diagram 510 comprises: SPA uses a threshold to automatically separate individual palpations within a body area. The therapist can then mark each palpation as "central", "unilateral left", or "unilateral right" (step 512); The therapist can enter one set of SOAP (Subjective, Objective, Assessment, and Plan) notes per session (step 514); SPA can compute a Pain-Force index (PFI) for each vertebra using the minimum force that caused pain an the pain level on NPRS scale: PFI=10−painLevel+minForce (lbs) (step 516; SPA computes a PFI for each vertebra with pain and generates a table of PFIs over all visits in this treatment (step 518); and SPA graphs all available PFIs for each vertebra to show the course of treatment (step 520).

Figure 11:
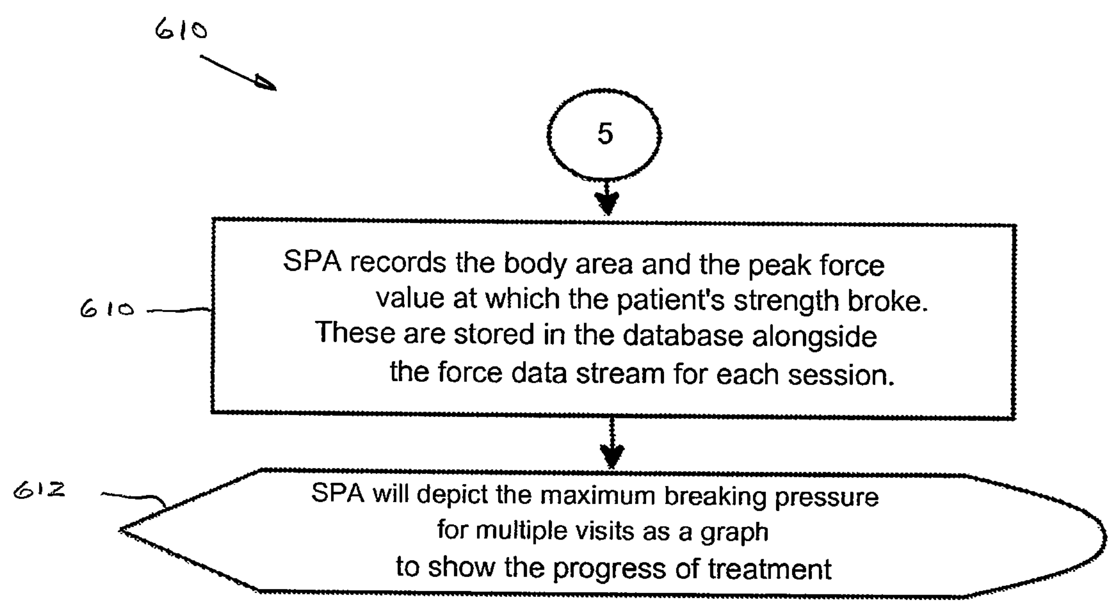
FIG. 11 is a Tested All muscle areas flow chart diagram (Flow Chart "5").

A Tested All muscle areas flow chart diagram 610 (Flow Chart "5") is shown in FIG. 11.

The Tested All muscle areas flow chart diagram 610 comprises: SPA records the body and the peak force value at which the patient's strength broke. These are store in the database alongside the force data stream for each session (step 610); and SPA will depict the maximum breaking pressure for multiple visits as a graph to show the progress of treatment (step 612).

Figure 12:
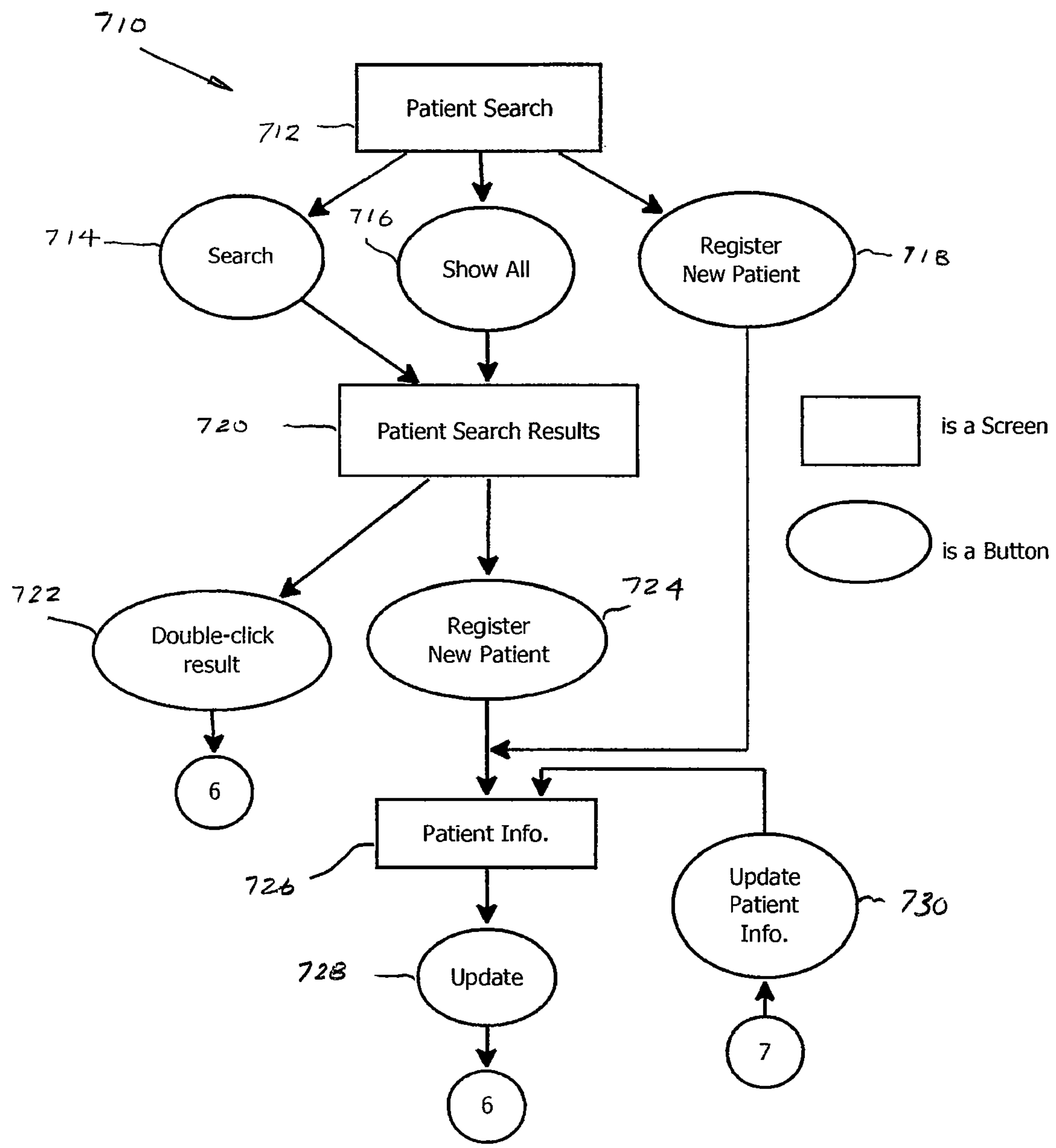
FIG. 12 is a Patient Search flow chart diagram.

A Patient Search flow chart diagram 710 is shown in FIG. 12.

The Patient Search flow chart diagram 710 comprises: Patient Search 712 (screen); Search 714 (button); Show All 716 (button); Register New Patient 718 (button); Patient Search Results 720 (screen); Double-click result 722 (button); Register New Patient 724 (button); Patient Info. 726 (screen); Update 728 (button); and Update Patient Info. (button).

Figure 13:
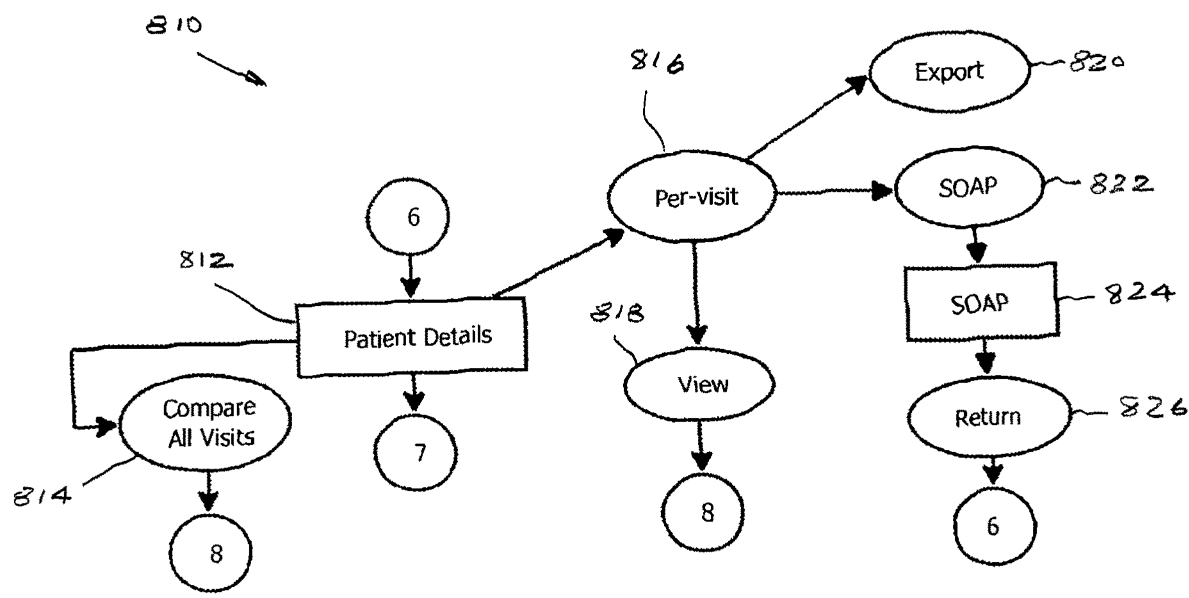
FIG. 13 is an Update flow chart diagram (Flow Chart "6").

An Update flow chart diagram 810 (Flow Chart "6") is shown in FIG. 13.

The Update flow chart diagram 810 comprises: Patient Details 812 (screen); Compare All Visits 814 (button); Per-visit 816 (button); View 818 (button); Export 820 (button); SOAP 822 (button); SOAP 824 (screen); Return 826 (button).

Figure 14:
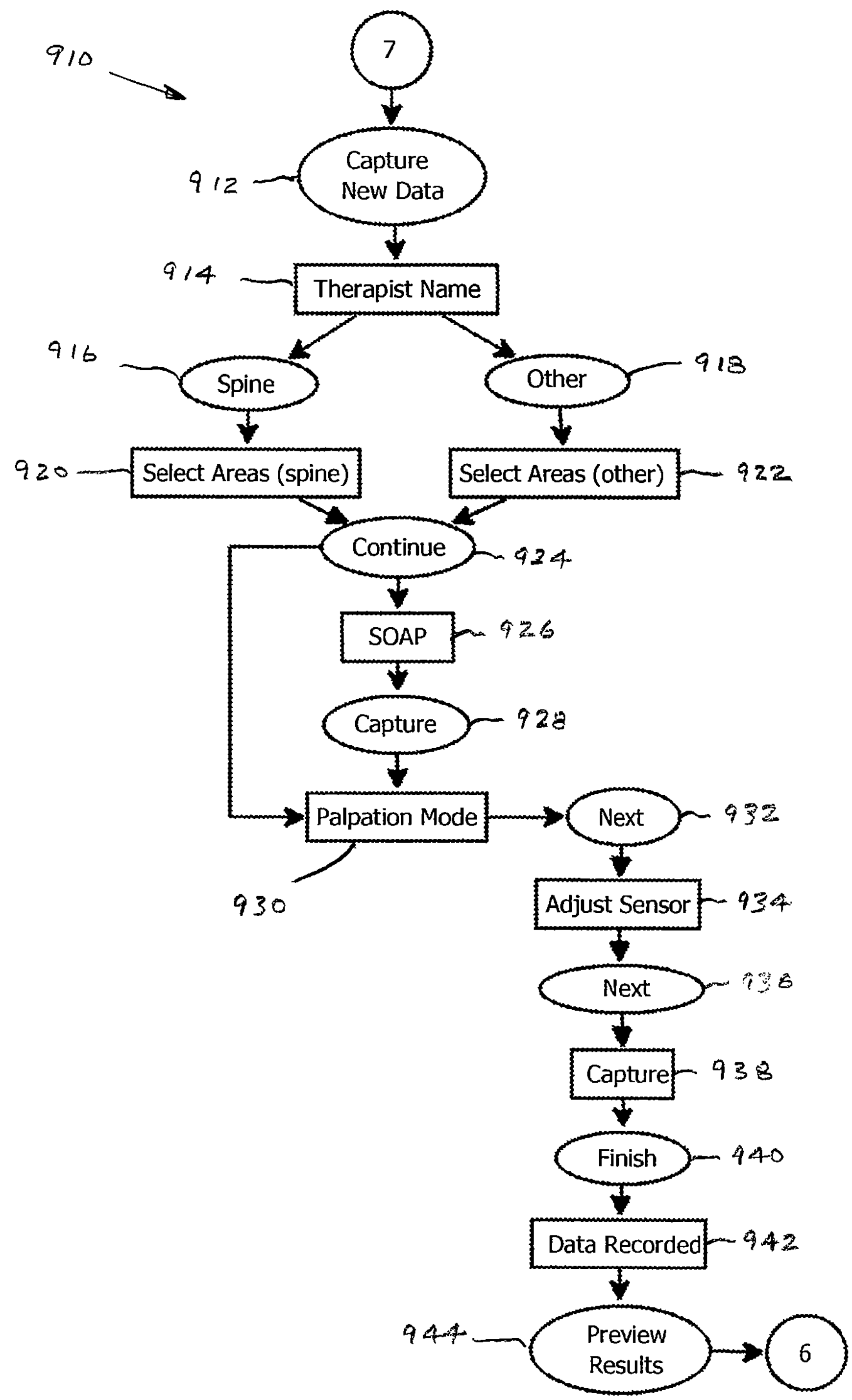
FIG. 14 is a Capture New Data flow chart diagram.

A Capture New Data flow chart diagram 910 (Flow Chart "7") is shown in FIG. 14.

The Capture New Data flow chart diagram 910 comprises: Capture New Data 912 (button); Therapist Name 914 (screen); Spine 916 (button); Other 918 (button); Select Areas (spine) 920 (display); Select Areas (other) 922 (display); Continue 924 (button); SOAP 926 (display); Capture 928 (button); Palpation Mode 930 (screen); Next 932 (button); Adjust Sensor 934 (screen); Next 936 (button); Capture 938 (screen); Finish 940 (button); Data Recorded 942 (screen); and Preview Results 944 (button).

Figure 15:
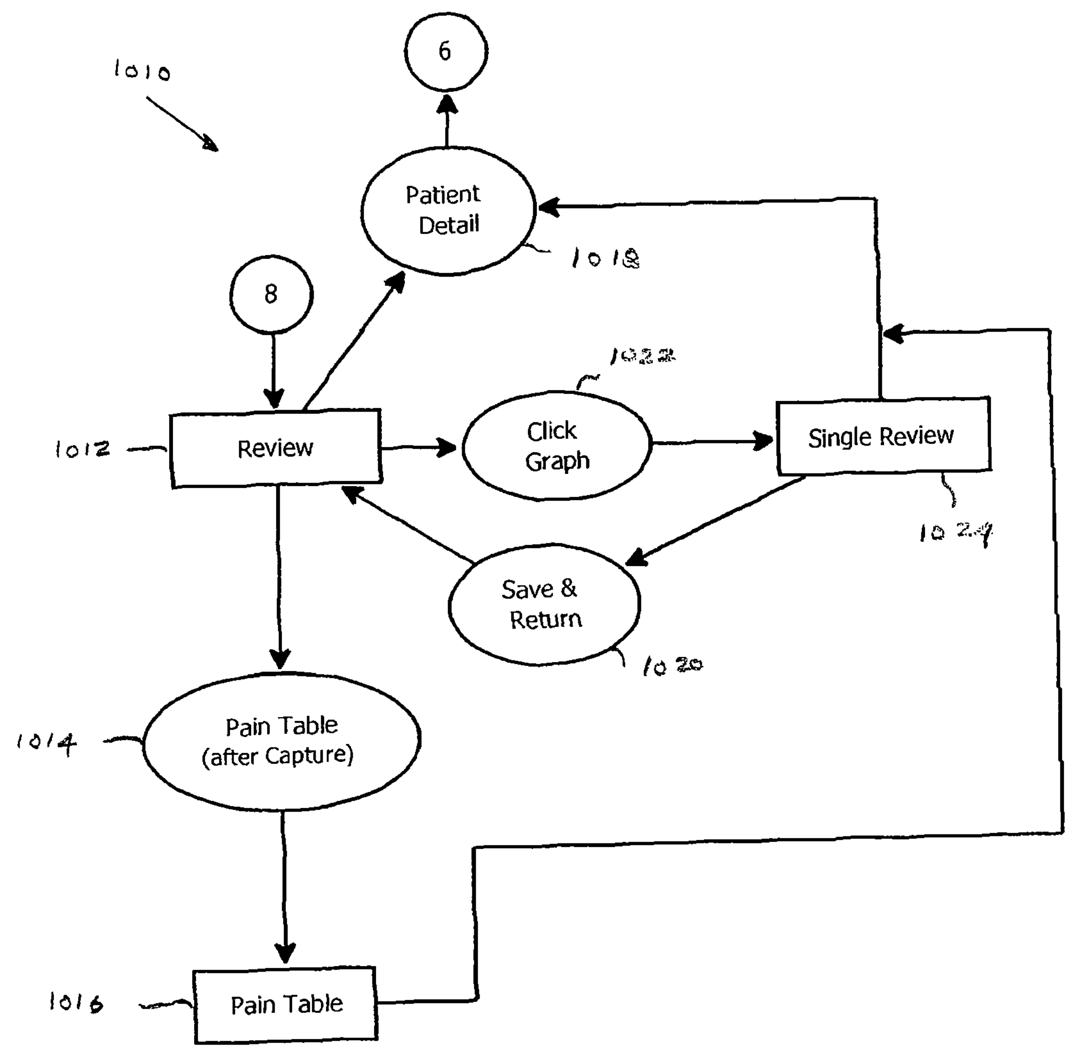
FIG. 15 is a Review flow chart diagram.

A Review flow chart diagram 1010 (Flow Chart "8") is shown in FIG. 15.

The Review flow chart diagram 1010 comprises: Review 1012 (screen); Pain Table (after Capture) 1014 (button); Pain Table 1016 (screen); Patient Detail 1018 (button); Save & Return 1020 (button); Click Graph 1022 (button); and Single Review 1024 (screen).

Thus, SPA provides objective data capture of pressures exerted during a patient evaluation using unobtrusive sensors and glove that do not interfere with the therapist's ability to diagnose, as well as a database with the recorded evaluation history for a patient at each step during treatment that is accessible during treatment and evaluation (baseline to multiple visits later).

SPA also allows for capturing at what time, and at what location during an examination the patient is experiencing pain, using a patient operated device. Using this information, SPA generates metrics about treatment progress and patient condition and concise evaluation reports that can be provided to physicians, patients to improve communication and patient treatment process. The collected data can also be used to provide evidence if a patient does or does not have a medical condition, including possible uses relating to legal cases or insurance fraud.

Unlike in the evaluations of the past, which involves subjective interpretation of each physical therapist about the severity of an injury, SPA provides more objective and unified data about the improvement of a patient, allowing for better therapist interoperability, better reporting techniques, decrease in medical record errors, and better data for planning a treatment. SPA also incorporates everything the therapist currently performs, allowing for the therapist to use his own judgment in combination with the presented information to determine what treatment to perform.

A method of objectifying palpation and/or pain can be provided. The method comprises the steps of palpating the patient with pressure or force measuring sensors, palpating with sensors on fingers, palm and/or pisiform area, transmitting force, pressure data from the sensors through a microprocessor to a computer, and analyzing the data using a software algorithm to compare the data against the norms of population and against the same patient over a period of time.

The method can include objectively recording the time the patient encounters pain using a wired or wireless switch to indicate pain when being palpated or touched by a care giver, providing patient the ability to click on a device to indicate pain multiple times; and capturing the subjective pain level of a patient on a NRPS scale after patient indicates pain.

The palpation evaluation or diagnosis system and method can be applied to the spine, or other parts of the body in various applications. For example, the palpation evaluation or diagnosis system can be applied for measuring muscle strength of a worker/patient's hand and/or legs. Manual muscle testing can then be objectified when the therapist wears an SPA glove device and pushes on the patient's body in specific directions. The SPA can measure the peak force needed to break the strength and the time it takes. The maximum forces, body part where the test is administered, and the directions can be stored in a database and compared over population norms and over a period of time with the same patient.

Use

The physical therapy glove device 12 is worn by a physical therapist when performing a palpation exam of a patient's spine or soft tissue. The physical therapy glove device 12 is double-layered, to isolate the sensors and electronics from both the physical therapist and the patient. The thumb pressure sensor 18*a* captures the force applied by the thumb, which is usually used on the upper parts of the spine. The side index finger pressure sensor 18*b* captures forces recorded when the therapist palpates with the side of the finger, normally used on the neck. The pressure sensor 18*c* on the back of the hand allows for easier progression through the examination. The pressure sensors 18*d,e* on the side of the hand are positioned to record pressure when palpating in a C-grip fashion, usually used on the lower parts of the spine.

During the exam, the patient is given the patient pain indicator device 14 and is instructed to push the button 14*a*, if he or she encounters pain. This information is transferred to the computer wirelessly and interpreted by the software package.

The software package interfaces to the physical therapy glove device 12 and patient pain indicator device 14, and records patient data generated during each evaluation session. When the therapist wears the physical therapy glove device 12, a validation mechanism is adopted to ensure the sensors are in the correct place. The therapist is asked to palpate a hard surface and apply pressures of 10 and 15 pounds on the thumb and pisiform area respectively to make sure the sensors are in the correct place. Once the physical therapist has logged in and entered the necessary information for a new patient, the software displays the view shown in FIG. 3.

The physical therapist can select to use one hand (GLV1) or two hands (GLV2) and selects the area they are planning to palpate (e.g. spine (SP) or a soft tissue (ST)). If the therapist selects spine (SEL1), he or she is further asked to specify which vertebra are going to be palpated in that area of the spine (SEL2). On subsequent visits, this data is auto-populated with the previous selections, but the physical therapist can add or remove vertebra as treatment progresses. When the vertebra to palpate has been selected, the physical therapist selects "continue" and the examination begins. The examination starts with the first vertebra selected in the list and proceeds to the next vertebra, until all of the vertebra have been evaluated.

During the examination, the graph of recorded pressures (G1) is shown in real time for the vertebra currently being palpated. If the patient presses the patient pain button device 14, an event is recorded (P11) as shown in FIG. 4, and the corresponding pressure for that pain is saved. If the pain button was pressed, when the physical therapist presses the pressure sensor 18*c*, the screen in FIG. 5 is shown.

The physical therapist asks the patient to rate the intensity of the pain on the standard scale (PI2) shown, and then enters the information either numerically or via mouse selection. At the conclusion of the examination, a report is generated showing the progress of each vertebra over the treatment progress. This report can be referenced in the saved patient history by other therapists, used to determine progress of treatment, or provide information to a third party, if necessary. The results are stored on the local computer, internal server and on the cloud. Patients, physicians and therapists can access the records on their smart phones, tablets or computers.

Example #1

Figure 16:
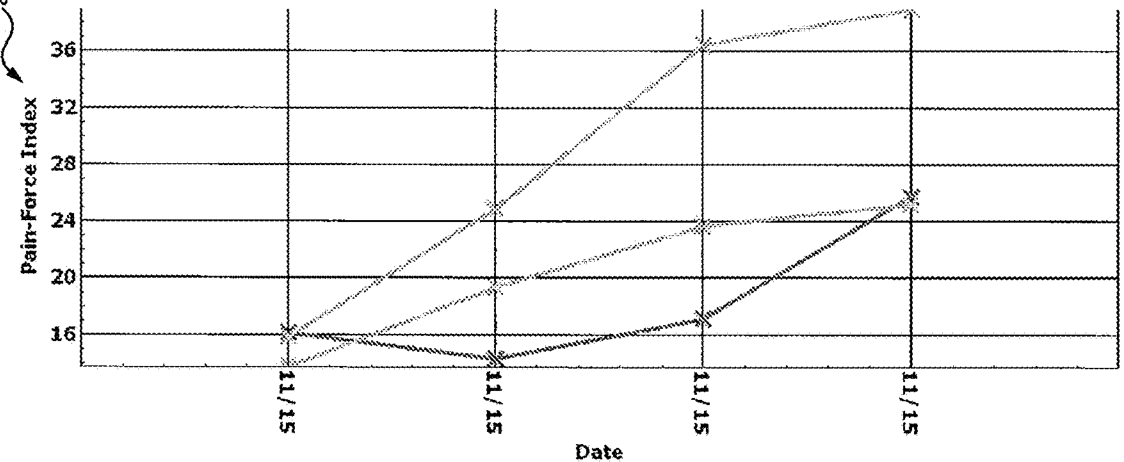
FIG. 16 shows Example #1 of a pain-force index report including graph of pain-force index verses date and table.

A pain-force index report 1210, including a pain-force index verses date graph 1220 and pain-force table 1230 is shown in FIG. 16.

The pain-force index report 1210 illustrates how a PFI would look like for multiple disks on spine. The PFI for each vertebra over multiple visits is captured in a report, which includes a combination of graphical representations and tabulated data of the patient's progress. The PFI report is attached to the treatment notes of the therapist, which can be used by a primary care physician, an orthopedic specialist, or to the insurance provider to better evaluate the patient progress. Observing the PFI values of a particular vertebra over time shows the effect and progress accomplished through the treatment plan. The PFI over multiple visits can be used to alter treatment plans if the current plan is not effective.

Example #2

Figure 17:
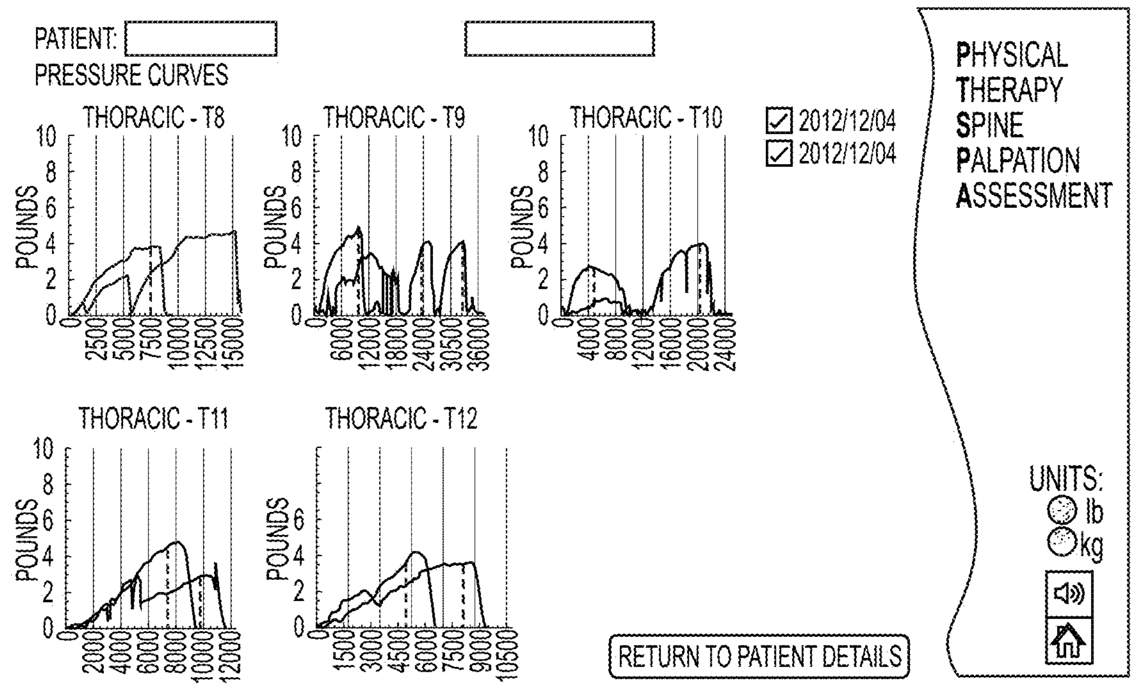
FIG. 17 shows Example #2 of pressure curves for a patient.

A therapist used the physical therapy glove device 12 (i.e. SPA glove) to palpate a stiff back of a patient, and the initial readings are shown in red on FIG. 17. The therapist administered the treatment for 15 minutes and the patient was palpated using the physical therapy glove device 12 and the final readings are shown in blue on FIG. 17. On the disks T9, T11 and T12 the patient showed improvement.

The specific methods and devices described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims.

As used herein and in the appended claims, the singular forms "a," "an," and "the" include plural reference unless the context clearly dictates otherwise. Under no circumstances may the patent application be interpreted to be limited to the specific examples or embodiments or methods specifically disclosed herein.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Although the present invention has been specifically disclosed by preferred embodiments and optional features, modification and variation of the concepts herein disclosed may be resorted to by those skilled in the art, and such modifications and variations are considered to be within the scope of this invention as defined by the appended claims. In addition, the invention has been described broadly and generically herein. Each of the narrower species and subgeneric groupings falling within the generic disclosure also form part of the invention.

DRAWINGS

10—Spine Palpation Assessment (SPA) system
12—physical therapy glove device
14—patient pain indicator device
14*a*—button (B1)
14*b*—button (B2)
14*c*—button (B3)
16—software package 16
18*a*—pressure sensor (PSI)
18*b*—pressure sensor (PS2)
18*c*—pressure sensor (PS3)
18*d*—pressure sensor (PS4)
18*e*—pressure sensor (PS5)
19—wire
20—microcontroller board (MC1)
22—USB cable (USB1)
24—computer
110—spine evaluation flow chart diagram
210—Spine flow chart diagram (Flow Chart "1")
310—Muscle Testing flow chart diagram (Flow Chart "2")
410—Soft Tissue flow chart diagram (Flow Chart "3")
510—All vertebrae palpated flow chart diagram
610—Tested All muscle areas flow chart diagram (Flow Chart "5")
710—Patient Search flow chart diagram
810—Update flow chart diagram (Flow Chart "6")
910—Capture New Data flow chart diagram
1010—Review flow chart diagram

I claim:

1. A glove system, comprising:

a computer; and a physical therapy or palpation glove device electrically connected to the computer, and comprising a glove comprising:

at least one layer of material;

a plurality of pressure sensors securely disposed with the at least one layer of material to be adjacent to a periphery of the glove, and a portion of the plurality of pressure sensors including (a) one or more first pressure sensors configured to detect one or more respective first pressures applied by a user's hand wearing the glove onto a vertebra or soft tissue of an individual and (b) one or more second pressure sensors disposed on a palm side of the glove to adjoin one or more portions of the periphery of the glove and configured to detect one or more respective second pressures applied by the user's hand when the user's hand wearing the glove is disposed in a C-grip configuration onto the vertebra or the soft tissue of the individual, and a microcontroller securely disposed with the glove, and electrically connected to the portion of the plurality of pressure sensors to (c) receive electrical signal inputs from the portion of the plurality of pressure sensors in which each of the received electrical signal inputs respectively corresponds to an amount of the respective detected pressure, and (d) generate respective output signals configured to be received by the computer and comprising the respective amounts of the detected pressures for display on the computer, wherein, in response to an application of a force applied from the user to at least one of the plurality of pressure sensors during the application of pressure onto the vertebra or the soft tissue of the individual, the at least one of the plurality of pressure sensors is electrically connected to the microcontroller and configured to generate, in response to receipt of the applied force from the user during the application of pressure onto the vertebra or the soft tissue of the individual and via the microcontroller, another output signal configured to be received by the computer and to cause the computer to display a scale comprising pain intensity ratings, and wherein the computer is configured to receive one or more of the output signals from the microcontroller of the glove device during the application of pressure onto the vertebra or the soft tissue of the individual.

2. The glove system according to claim 1, wherein the computer is located remotely relative to the glove device.

* * * * *